US012788297B2

(12) United States Patent
Watanabe

(10) Patent No.: US 12,788,297 B2
(45) Date of Patent: Nov. 10, 2026

(54) ELECTRIC SIGNAL TRANSMISSION DEVICE AND ELECTRIC SIGNAL TRANSMISSION DEVICE OPERATION METHOD

(71) Applicant: Masataka Watanabe, Tokyo (JP)

(72) Inventor: Masataka Watanabe, Tokyo (JP)

(73) Assignee: Masataka Watanabe, Tokyo (JP)

( * ) Notice: Subject to any disclaimer, the term of this patent is extended or adjusted under 35 U.S.C. 154(b) by 964 days.

(21) Appl. No.: 17/995,835

(22) PCT Filed: Apr. 1, 2021

(86) PCT No.: PCT/JP2021/014121
§ 371 (c)(1),
(2) Date: Oct. 7, 2022

(87) PCT Pub. No.: WO2021/205976
PCT Pub. Date: Oct. 14, 2021

(65) Prior Publication Data

US 2023/0148933 A1 May 18, 2023

(30) Foreign Application Priority Data

Apr. 9, 2020 (JP) ................................ 2020-070267

(51) Int. Cl.
*A61B 5/294* (2021.01)
*A61B 5/24* (2021.01)
*A61B 5/293* (2021.01)
*G01R 19/00* (2006.01)

(52) U.S. Cl.
CPC ................ *A61B 5/293* (2021.01); *A61B 5/24* (2021.01); *A61B 5/294* (2021.01); *G01R 19/0046* (2013.01); *A61B 2503/12* (2013.01); *A61B 2562/0209* (2013.01)

(58) Field of Classification Search
CPC ........... A61B 5/293; A61B 5/294; A61B 5/24; A61B 2503/12; A61B 2562/0209; G01R 19/0046
See application file for complete search history.

(56) References Cited

U.S. PATENT DOCUMENTS

2013/0090706 A1* 4/2013 Nudo ................ A61N 1/36103 607/62
2013/0253606 A1* 9/2013 Youn ...................... A61F 2/583 607/48
2015/0141786 A1* 5/2015 Durand ................. A61B 5/388 607/116
2015/0217109 A1* 8/2015 Achyuta ................. A61B 5/24 607/116

(Continued)

OTHER PUBLICATIONS

Willand, Michael, et. al., "Electrical Stimulation to Promote Peripheral Nerve Regeneration", Neurorehabilitation and Neural Repair, 2016 (Year: 2016).*

(Continued)

*Primary Examiner* — Adam Z Minchella
(74) *Attorney, Agent, or Firm* — Studebaker Brackett PLLC

(57) ABSTRACT

An electric signal transmission device including an electrode 11, disposed to be opposed to an electrogenic cell, and for sending and receiving electric signals to and from the electrogenic cell via the electrode 11.

9 Claims, 3 Drawing Sheets

(56) References Cited

U.S. PATENT DOCUMENTS

| | | | | |
|---|---|---|---|---|
| 2019/0017988 A1* | 1/2019 | Wijdenes | ............... | A61B 5/291 |
| 2019/0286592 A1 | 9/2019 | Seo et al. | | |
| 2022/0249834 A1* | 8/2022 | Serex | ..................... | A61B 5/388 |

OTHER PUBLICATIONS

International Search Report issued in PCT/JP2021/014121; mailed Jun. 22, 2021.
Ogi, Jun et al.; "A 4.8-μVrms-Noise CMOS-Microelectrode Array With Density-Scalable Active Readout Pixels via Disaggregated Differential Amplifier Implementation"; Frontiers in Neuroscience; Mar. 2019; vol. 13; Article 234; pp. 1-6.
Nistor, Paul A. et al.; "Long-term culture of pluripotent stem-cell-derived human neurons on diamond—A substrate for neurodegeneration research and therapy"; Biomaterials 61; 2015; pp. 139-149.
Fujie, Toshinori et al.; "Engineered Nanomembranes for Directing Cellular Organization Toward Flexible Biodevices"; Nano Letters; 2013; 13; pp. 3185-3192.
Sato, Hiroki et al.; "Microfabric Vessels for Embryoid Body Formation and Rapid Differentiation of Pluripotent Stem Cells"; Scientific Reports; 6:31063; doi: 10.1038/srep31063; 2016; pp. 1-13.
Khankan, Rana R. et al.; "Olfactory Ensheathing Cell Transplantation after a Complete Spinal Cord Transection Mediates Neuroprotective and Immunomodulatory Mechanisms to Facilitate Regeneration"; The Journal of Neuroscience; Jun. 8, 2016; 36(23); pp. 6269-6286.
Steinbeck, Julius A. et al.; "Functional connectivity under optogenetic control allows modeling of human neuromuscular disease"; Cell Stem Cell; Jan. 7, 2016; 18(1); doi:10.1016/j.stem.2015.10.002; total 18 pgaes.
Willand, Michael P. et al.; "Electrical Stimulation to Promote Peripheral Nerve Regeneration"; Neurorehabilitation and Neural Repair; 2016; vol. 30(5); pp. 490-496.
Musk, Elon et al.; "An Integrated Brain-Mchine Interface Platform with Thousands of Channels"; bioRxiv 703801; doi: https://doi.org/10.1101/703801; total 12 pages.
Histed, Mark H. et al.; "Direct Activation of Sparse, Distributed Populations of Cortical Neurons by Electrical Microstimulation"; Neuron 63; Aug. 27, 2009; pp. 508-522.
Davies, Stephen J. A. et al.; "Long Interfascicular Axon Growth from Embryonic Neurons Transplanted into Adult Myelinated Tracts"; The Journal of Neuroscience; Mar. 1994; 14(3): total 18 pages.
International Preliminary Report on Patentability (Chapter I) and Written Opinion of the International Searching Authority issued in PCT/JP2021/014121; issued Oct. 6, 2022.

* cited by examiner

ELECTRIC SIGNAL TRANSMISSION DEVICE AND ELECTRIC SIGNAL TRANSMISSION DEVICE OPERATION METHOD

TECHNICAL FIELD

The present invention relates to an electric signal transmission technique and relates to an electric signal transmission device and an electric signal transmission device operation method.

BACKGROUND ART

A brain-machine interface that connects a brain and a machine has been developed (see, for example, Patent Literature 1). In noninvasive methods, such as electroencephalography and transcranial magnetic stimulation (TMS), activities of cranial nerves cannot be precisely studied. Therefore, an invasive interface embedded in the brain is necessary. For example, in the Defense Advanced Research Project Agency (DARPA) of the United States, a microwire is inserted into a brain, activities of nerve cells are recorded, and the nerve cells are stimulated.

CITATION LIST

Patent Literature

Patent Literature 1: United States Patent Application Publication No. 2019/0286592

SUMMARY OF THE INVENTION

Technical Problem

There have been demands for means capable of efficiently measuring the activities of various electrogenic cells in an invasive or noninvasive manner. Therefore, the target of the present invention is to provide an electric signal transmission device and an electric signal transmission device operation method capable of efficiently sending and receiving electric signals to and from cells.

Solution to Problem

According to an aspect of the present invention, there is provided an electric signal transmission device operation method including receiving, by an electric signal transmission device that is arranged outside a body and opposed to an axon of a nerve cell, an electric signal derived from the axon, wherein the electric signal transmission device includes an electrode, and the electrode receives the electric signal derived from the axon. The method may be carried out in vitro.

According to an aspect of the present invention, there is provided an electric signal transmission device operation method including sending, by an electric signal transmission device that is arranged outside a body and opposed to an axon of a nerve cell, an electric signal to the axon, wherein the electric signal transmission device includes an electrode, and the electrode sends the electric signal to the axon. The method may be carried out in vitro.

According to an aspect of the present invention, there is provided an electric signal transmission device operation method including receiving, by an electric signal transmission device opposed to an axon of a nerve cell inside a body, an electric signal derived from the axon, wherein the electric signal transmission device includes an electrode, and the electrode receives the electric signal derived from the axon. The method may be carried out in vivo.

According to an aspect of the present invention, there is provided an electric signal transmission device operation method including emitting an electric signal by an electric signal transmission device opposed to an axon of a nerve cell inside a body, wherein the electric signal transmission device includes an electrode, and the electrode emits the electric signal. The method may be carried out in vivo.

In the electric signal transmission device operation method described above, the electric signal transmission device may further include an arranged cell arranged on the electrode and opposed to the axon.

In the electric signal transmission device operation method described above, the electric signal transmission device may further include an arranged cell arranged on the electrode and opposed to the axon, and the arranged cell may transmit the electric signal from the axon to the electrode.

In the electric signal transmission device operation method described above, the electric signal transmission device may further include an arranged cell arranged on the electrode and opposed to the axon, and the arranged cell may transmit the electric signal from the electrode to the axon.

In the electric signal transmission device operation method described above, the electric signal transmission device may further include an arranged cell arranged on the electrode and opposed to the axon, and the arranged cell may transmit the electric signal emitted by the electrode.

In the electric signal transmission device operation method described above, the electric signal transmission device may further include a cell retention membrane in which a recess located on the electrode is provided, and the arranged cell may be arranged in the recess of the cell retention membrane.

In the electric signal transmission device operation method described above, the arranged cell may be a muscle cell.

In the electric signal transmission device operation method described above, the arranged cell may be a nerve cell.

In the electric signal transmission device operation method described above, the arranged cell may be opposed to an end portion of the axon.

In the electric signal transmission device operation method described above, the electrode may be opposed to an end portion of the axon.

In the electric signal transmission device operation method described above, the end portion of the axon may be a cut part of the axon.

In the electric signal transmission device operation method described above, the end portion of the axon may be an end portion of a part extending from a cut part of the axon.

In the electric signal transmission device operation method described above, the axon may be included in a nerve fascicle.

In the electric signal transmission device operation method described above, the axon may be included in a central nervous system.

In the electric signal transmission device operation method described above, the axon may be included in a brain.

In the electric signal transmission device operation method described above, the axon may be included in a nerve fascicle connecting two hemispheres.

In the electric signal transmission device operation method described above, the axon may be included in a spinal cord.

In the electric signal transmission device operation method described above, the axon may be included in a peripheral nervous system.

In the electric signal transmission device operation method described above, the electric signal transmission device may be inserted into a nerve fascicle.

According to an aspect of the present invention, there is provided an electric signal transmission device operation method including receiving, by an electric signal transmission device that includes an electrode and a first nerve cell arranged on the electrode and is arranged outside a body, an electric signal derived from a second nerve cell outside the body, wherein a synapse of an axon distal end of the first nerve cell is synapse-coupled to the second nerve cell, and the electrode receives the electric signal derived from the second nerve cell. The method may be carried out in vitro.

According to an aspect of the present invention, there is provided an electric signal transmission device operation method including sending, by an electric signal transmission device that includes an electrode and a first nerve cell arranged on the electrode and is arranged outside a body, an electric signal to a second nerve cell outside the body, wherein a synapse of an axon distal end of the first nerve cell is synapse-coupled to the second nerve cell, and the electrode sends the electric signal to the second nerve cell. The method may be carried out in vitro.

According to an aspect of the present invention, there is provided an electric signal transmission device operation method including receiving, by an electric signal transmission device that includes an electrode and a first nerve cell arranged on the electrode and is arranged inside a body, an electric signal derived from a second nerve cell inside the body, wherein a synapse of an axon distal end of the first nerve cell is synapse-coupled to the second nerve cell, and the electrode receives the electric signal derived from the second nerve cell. The method may be carried out in vivo.

According to an aspect of the present invention, there is provided an electric signal transmission device operation method including emitting an electric signal by an electric signal transmission device that includes an electrode and a first nerve cell arranged on the electrode and is arranged inside a body, wherein a synapse of an axon distal end of the first nerve cell is synapse-coupled to a second nerve cell inside the body, and the electrode emits the electric signal. The method may be carried out in vivo.

In the electric signal transmission device operation method described above, the electric signal transmission device may further include a cell retention membrane in which a recess located on the electrode is provided, and the first nerve cell may be arranged in the recess of the cell retention membrane.

In the electric signal transmission device operation method described above, the second nerve cell may be included in a central nervous system.

In the electric signal transmission device operation method described above, the second nerve cell may be included in a brain.

In the electric signal transmission device operation method described above, the second nerve cell may be included in a spinal cord.

In the electric signal transmission device operation method described above, the second nerve cell may be included in a peripheral nervous system.

In the electric signal transmission device operation method described above, the electric signal transmission device may be inserted into a nerve fascicle.

According to an aspect of the present invention, there is provided an electric signal transmission device including an electrode, disposed to be opposed to an electrogenic cell, and for sending and receiving electric signals to and from the electrogenic cell via the electrode.

The electric signal transmission device described above may further include a cell retention membrane in which a recess located on the electrode is provided.

The electric signal transmission device described above may further include an arranged cell arranged on the electrode and opposed to the electrogenic cell.

In the electric signal transmission device described above, the arranged cell may be a muscle cell.

In the electric signal transmission device described above, the arranged cell may be a nerve cell.

In the electric signal transmission device described above, the arranged cell may transmit the electric signal transmitted from the electrogenic cell to the electrode.

In the electric signal transmission device described above, the arranged cell may transmit the electric signal emitted from the electrode to the electrogenic cell.

In the electric signal transmission device described above, the electrogenic cell may be at least one selected from a nerve cell and a cardiac muscle cell.

In the electric signal transmission device described above, the electrogenic cell may be a nerve cell, and the arranged cell may be opposed to an end portion of an axon of the nerve cell.

In the electric signal transmission device described above, the electrogenic cell may be a nerve cell, and the electrode may be opposed to an end portion of an axon of the nerve cell.

The electric signal transmission device described above may be an electric signal transmission device to be inserted into a nerve fascicle.

In the electric signal transmission device described above, the electrode may be included in an electrode array.

In the electric signal transmission device described above, the electrode array may be included in an integrated circuit.

Advantageous Effects of Invention

According to the present invention, it is possible to provide an electric signal transmission device and an electric signal transmission device operation method capable of efficiently sending and receiving electric signals to and from a cell.

DESCRIPTION OF EMBODIMENT

Figure 1:
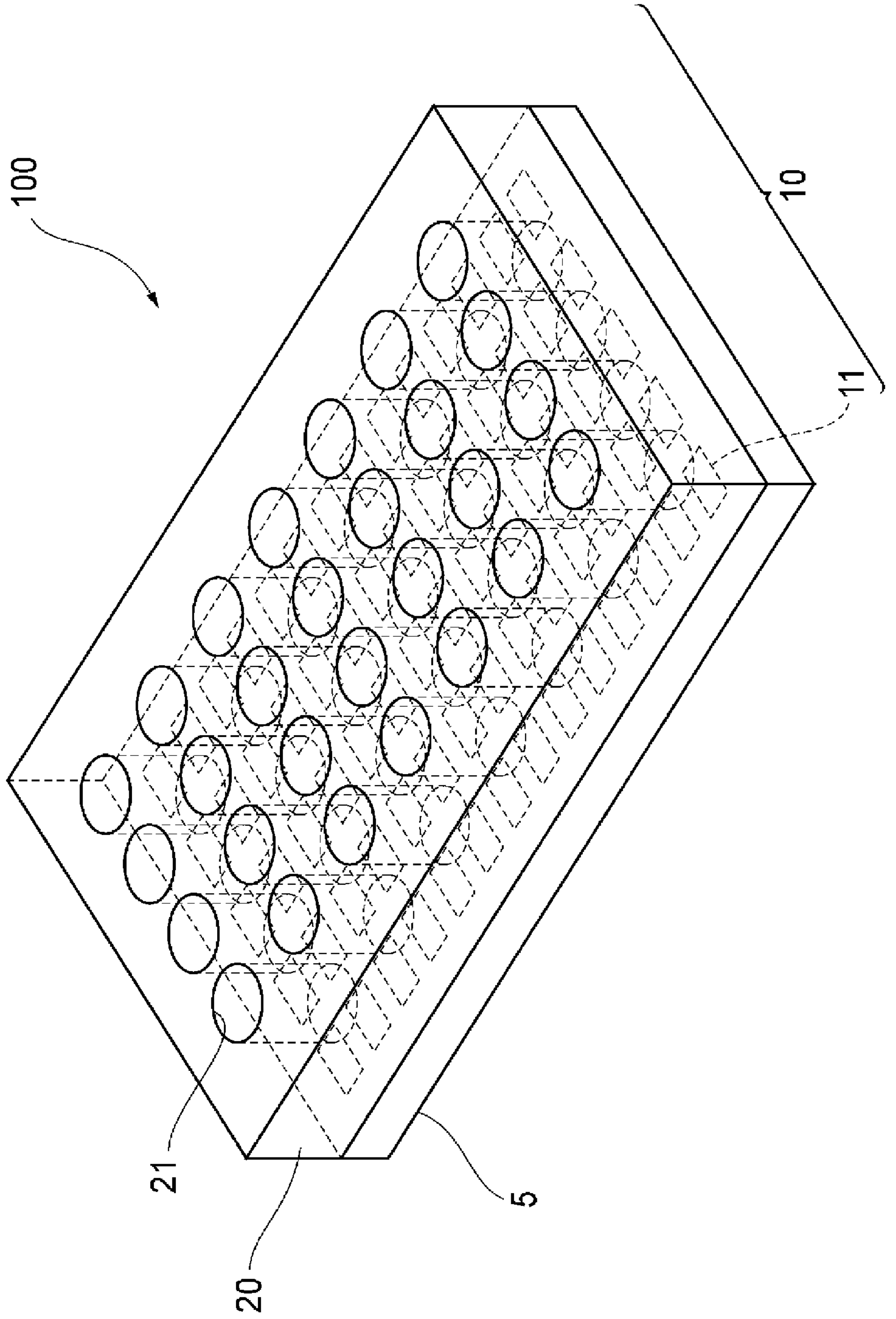
FIG. 1 is a schematic diagram of an electric signal transmission device according to an embodiment.

An embodiment of the present invention is described below. In the following description of the drawings, the same or similar portions are denoted by the same or similar reference numerals and signs. However, the drawings are schematic. Therefore, specific dimensions and the like should be determined by checking the following explanation. It goes without saying that, even among the drawings, portions having different relations and ratios of dimensions thereof are included.

As shown in FIG. 1, an electric signal transmission device 100 according to the embodiment includes a substrate 5 and an electrode 11 provided on the substrate 5. The electric signal transmission device 100 is disposed to be opposed to an electrogenic cell and used to send and receive electric signals to and from the electrogenic cell via the electrode 11. The electric signal transmission device 100 may include a plurality of electrodes 11. The plurality of electrodes 11 may configure an electrode array 10.

The electrode 11 is opposed to the electrogenic cell. A cell may be arranged on the substrate 5 and the electrode 11. A plurality of cells may be arranged on the substrate 5 and the electrode 11. The arranged cell on the electrode 11 may be opposed to the electrogenic cell.

The electric signal transmission device 100 may further include a cell retention membrane 20 covering the electrode array 10. A recess 21 capable of storing the cell arranged on the substrate 5 and the electrode 11 may be provided in the cell retention membrane 20.

The electric signal transmission device 100 according to the embodiment is used to receive, in the electrode 11, for example, an electric signal transmitted from the electrogenic cell. The electric signal transmission device 100 according to the embodiment is used to send, for example, an electric signal emitted from the electrode 11 to the electrogenic cell.

In the electric signal transmission device 100 according to the embodiment, for example, an electric signal from the electrogenic cell may be received by the electrode 11 via the arranged cell arranged on the electrode 11. However, the electric signal from the electrogenic cell may be received by the electrode 11 not via the arranged cell. In the electric signal transmission device 100 according to the embodiment, for example, the electric signal from the electrode 11 may be sent to the electrogenic cell via the arranged cell arranged on the electrode 11. However, the electric signal from the electrode 11 may be sent to the electrogenic cell not via the arranged cell.

Examples of the electrogenic cell are not particularly limited but include a nerve cell and a cardiac muscle cell. In the following explanation, an example is described in which the electrogenic cell is the nerve cell.

The plurality of electrodes 11 of the electrode array 10 are capable of sending and receiving electric signals independently from one another. The electrode array 10 is included in, for example, an integrated circuit. An example of the integrated circuit is a large scale integrated circuit (LSI). Examples of the LSI include a complementary metal oxide semiconductor (CMOS) circuit. In the CMOS, a P-channel MOS field effect transistor (FET) and an N-channel MOSFET are connected.

Figure 2:
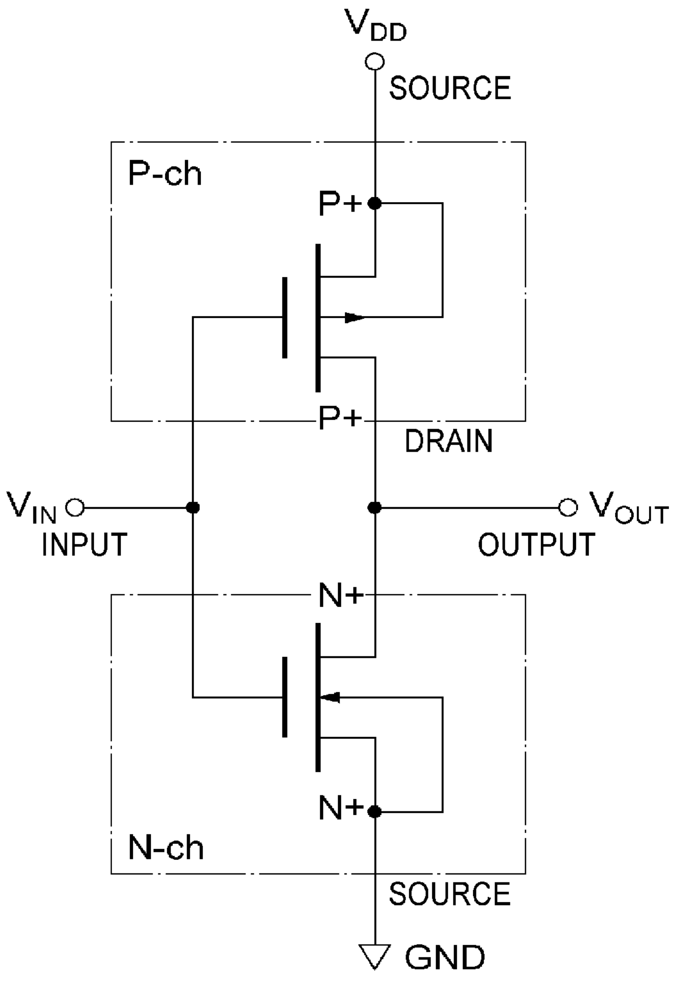
FIG. 2 is a schematic diagram of a CMOS according to the embodiment.

An equivalent circuit of the CMOS is shown in FIG. 2. Each of the plurality of electrodes of the electrode array 10 is connected to a gate electrode of the P-channel MOSFET and a gate electrode of the N-channel MOSFET. An output voltage $V_{OUT}$ is output from a drain of the P-channel MOSFET or the N-channel MOSFET according to an input voltage VIN to the gate electrodes of the P-channel MOSFET and the N-channel MOSFET. Conversely, a voltage can be output from each of the plurality of electrodes of the electrode array 10 according to an input voltage to the drain of the P-channel MOSFET or the N-channel MOSFET.

The electrode array 10 is connected to, for example, a computer system. An electric signal received by the electrode 11 of the electrode array 10 is, for example, amplified and transmitted to the computer system. The computer system controls the electrode array 10 and sends the electric signal from the electrode 11 (see, for example, Jun Ogi et al., "A 4.8-mVrms-Noise CMOS-Microelectrode Array With Density-Scalable Active Readout Pixels via Disaggregated Differential Amplifier Implementation," Frontiers in Neuroscience, March 2019|Volume 13|Article 234).

A pitch of the electrodes 11 in the electrode array 1 shown in FIG. 1 is optional. For example, in the electric signal transmission device 100 according to the embodiment, when electric signals are sent to and received from an axon of the nerve cell, the pitch of the electrodes 11 is preferably smaller than the diameter of the axon of the nerve cell. The diameter of an axon of a nerve cell of a mammal is from 0.5 μm to 20 μm and the diameter of an axon seen on a corpus callosum section of a human is approximately 10 μm. By setting the pitch of the electrodes smaller than the diameter of the axon of the nerve cell, a plurality of axons are prevented from becoming electrically communicable to one electrode.

The material of the cell retention membrane 20 is not particularly limited. The material of the cell retention membrane 20 is selected from, for example, materials not having cytotoxicity and having cellular affinity. Examples of the material of the cell retention membrane 20 include synthetic resin, glass, and diamond. Examples of the synthetic resin include polystyrene. The diamond may be polycrystal diamond including small crystals (see, for example, Paul A. Nistor et al., "Long-term culture of pluripotent stem-cell-derived human neurons on diamond e A substrate for neurodegeneration research and therapy," Biomaterials 61 (2015) 139e149).

The shape of each of a plurality of recesses 21 provided in the cell retention membrane 20 is not particularly limited. An opening of the recess 21 may be circular or may be polygonal. The width and the depth of the recess 21 are set according to the size of the arranged cell stored in the recess 21.

The surface of the electrode 11 and the inside of the recess 21 of the cell retention membrane 20 may be coated with a matrix for improving adhesion and extensibility of a cell. Example of the matrix include I-type collagen, IV-type collagen, fibronectin, laminin, Matrigel, poly-D-lysine, poly-L-lysine, poly-L-ornithine, and gelatin. A carbon nanotube may be incorporated in fibronectin to form a nanopattern on the surface of the cell retention membrane 20 (see, for example, Toshinori Fujie et al., "Engineered Nanomembranes for Directing Cellular Organization Toward Flexible Biodevices," Nano Lett. 2013, 13, 3185 to 3192).

The length from the bottom surface of the recess 21 of the cell retention membrane 20 to the electrode 11 and the material of the cell retention membrane 20 are set such that the arranged cell stored in the recess 21 of the cell retention membrane 20 and the electrode located below the arranged cell are capable of electrically communicating.

Examples of the arranged cell include a nerve cell and a muscle cell. Examples of the nerve cell include an olfactory ensheathing cell. It is preferable that a single-cell arranged cell is stored in one recess 21 (see, for example, Sato, H. et al. Microfabric Vessels for Embryoid Body Formation and Rapid Differentiation of Pluripotent Stem Cells. Sci. Rep. 6, 31063; doi: 10.1038/srep31063 (2016)). One arranged cell may be arranged on the substrate 5 across the plurality of electrodes 11.

The arranged cell may be electrically connected to an axon of the nerve cell. The arranged cell and the axon of the nerve cell may be connected such that electric signals can be sent and received. The arranged cell and the axon of the nerve cell do not always need to be directly connected if the sending and receiving of electric signals are possible. A gap may be present between the arranged cell and the axon of the nerve cell. An electric signal from the axon of the nerve cell may be received by the electrode 11 via the arranged cell or may be received by the electrode 11 not via the arranged cell. An electric signal emitted by the electrode 11 may be sent to the axon of the nerve cell via the arranged cell or may be sent to the axon of the nerve cell not via the arranged cell.

When the arranged cell is the nerve cell, the diameter of the nerve cell is 3 μm or more and 18 μm or less. The diameter of the axon seen on the corpus callosum section of the human is approximately 10 μm. Therefore, approximately one arranged cell is connected to one axon.

Subsequently, a method for operating the electric signal transmission device 100 according to the embodiment is described.

Figure 3:
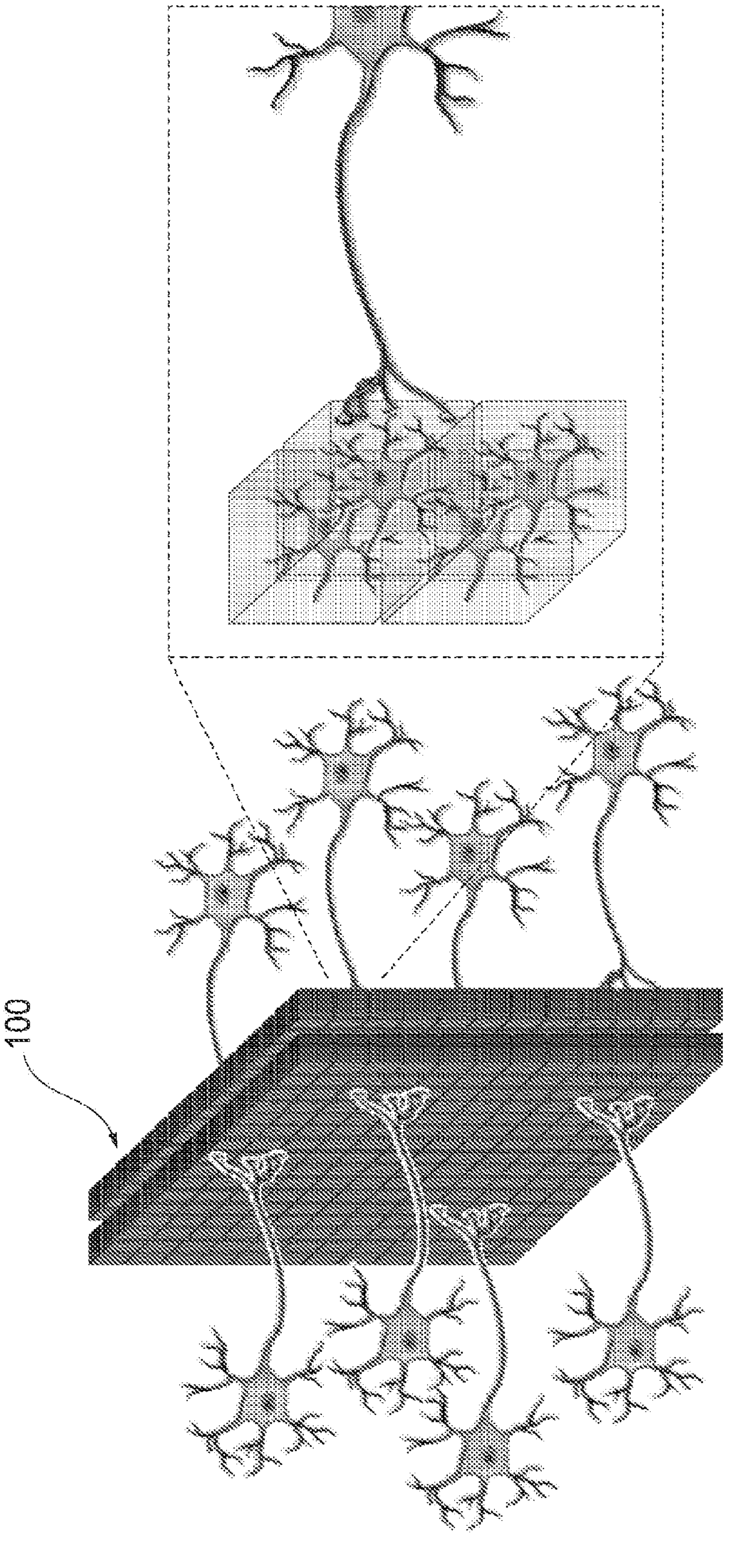
FIG. 3 is a schematic diagram of the electric signal transmission device according to the embodiment.

A nerve fascicle connecting a left hemisphere and a right hemisphere is cut. The nerve fascicle is any one of a corpus callosum, an anterior commissure, and a posterior commissure, for example. As shown in FIG. 3, two electric signal transmission devices 100 are inserted into a cut part of the nerve fascicle. Both the electric signal transmission devices 100 are inserted into the cut part of the nerve fascicle such that the arranged cell is opposed to a cut section of the nerve fascicle.

Among axons included in the cut nerve fascicle, an axon on a synapse side undergoes necrosis because the axon is cut off from a cell nucleus. However, among the axons included in the cut nerve fascicle, regeneration from damage of an axon on a cell side is accelerated by the arranged cell of the electric signal transmission device 100 opposed to an axon section.

For example, when the arranged cell is the olfactory ensheathing cell, the olfactory ensheathing cell urges regeneration of an axon (see, for example, Rana R. Khankan et al., "Olfactory Ensheathing Cell Transplantation after a Complete Spinal Cord Transection Mediates Neuroprotective and Immunomodulatory Mechanisms to Facilitate Regeneration," The Journal of Neuroscience, Jun. 8, 2016, 36 (23): 6269 to 6286).

When the arranged cell is the muscle cell, a neuromuscular junction is formed between an axon end portion on the cell side and the muscle cell (see, for example, Julius A. Steinbeck et al., "Functional connectivity under optogenetic control allows modeling of human neuromuscular disease," Cell Stem Cell. 2016 Jan. 7; 18 (1): 134 to 143. doi: 10.1016/j.stem.2015.10.002).

The axon on the cell side is also regenerated by applying an electric stimulus to the axon on the cell side by emitting an electric signal from the electrode of the electrode array 10 and sending the electric signal to the axon on the cell side via the cell retention membrane 20 and the arranged cell (see, for example, Michael P. Willand et al., "Electrical Stimulation to Promote Peripheral Nerve Regeneration," Neurorehabilitation and Neural Repair 2016, Vol. 30 (5) 490 to 496).

When the nerve cell is stimulated in the hemisphere, active potential, which is an electric signal, is transmitted through the axon. The electric signal is transmitted from the end portion of the axon to the electrode 11 of the electrode array 10. The end portion of the axon may be a cut part of the axon or may be the end portion of a part extended from the cut part of the axon. Consequently, the electric signal transmission device 100 is capable of receiving the active potential of the nerve cell. When information is to be recorded in the hemisphere, the electrode 11 of the electrode array 10 of the electric signal transmission device 100 emits an electric signal. The electric signal emitted from the electrode 11 is sent to the axon. In this case, in the axon, the electric signal is antidromically transmitted to a cell body.

If a plurality of electrodes are inserted into a grey matter to attempt to read out information in nerve cells at high density, since cell bodies of the nerve cells are densely present in the grey matter, the inserted plurality of electrodes are likely to break the cell bodies of the nerve cells and affect a brain function. In the grey matter, since the cell bodies of the nerve cells are three-dimensionally densely present, it is extremely difficult to electrically connect electrodes to the individual nerve cells without affecting adjacent nerve cells and read out electric signals from the individual nerve cells (see, for example, Elon Musk et al., "An integrated brain-machine interface platform with thousands of channels," bioRxiv 703801; doi: https://doi.org/10.1101/703801).

When an electric stimulus is applied to a cell body of a certain nerve cell by an electrode, the electric stimulus is also applied to an axon of another nerve cell present near the cell body. Therefore, a stimulus is applied to a nerve cell far from the nerve cell to which the electric stimulus is about to be applied. In this case, the brain is likely to show a reaction different from a reaction shown when only the target nerve cell is stimulated. Since only a nerve cell that receives an electric signal cannot be stimulated by the electrode, information cannot be read from and written in a specific nerve cell (see, for example, Mark H. Histed et al., "Direct Activation of Sparse, Distributed Populations of Cortical Neurons by Electrical Microstimulation," Neuron 63, 508 to 522, Aug. 27, 2009).

In contrast, with the method for operating the electric signal transmission device 100 according to the embodiment, since the electrode is inserted into not the grey matter but the nerve fascicle between the left and right hemispheres, cell bodies in the grey matter is not broken. In the cut axon, although the axon on the synapse side undergoes necrosis, the axon on the cell body side is regenerated from damage by the arranged cell. Therefore, the nerve cell is capable of continuing to function even after the electric signal transmission device 100 is disposed in the cut part of the axon.

Note that the arranged cell may not be arranged on the substrate 5 and the electrode 11 and a substance for accelerating the regeneration of the axon from the damage may be disposed on the substrate 5 and the electrode 11.

With the method for operating the electric signal transmission device 100 according to the embodiment, approximately one arranged cell is connected to one axon. Therefore, it is possible to apply an electric stimulus from the electrode, which receives the active potential from the axon, to the same axon. Therefore, inconsistency of reading and writing of information does not occur. It is possible to write highly accurate information in the brain.

In the example described above, the axon opposed to the electric signal transmission device 100 is included in the brain. However, the axon opposed to the electric signal transmission device 100 may be included in a central nervous system other than the brain. For example, the axon opposed to the electric signal transmission device 100 may be included in a spinal cord. The axon opposed to the electric signal transmission device 100 may be included in a peripheral nervous system. For example, a sensation and a motion of a body may be controlled and internal organs and blood vessels may be controlled by sending and receiving electric signals to and from an axon of the peripheral nervous system using the electric signal transmission device 100. The cut of the axon may be a cut due to an accident.

Subsequently, a method for operating the electric signal transmission device 100 according to another embodiment is described.

A nerve fascicle connecting a left hemisphere and a right hemisphere is cut. Two electric signal transmission devices 100 are inserted in a cut part of the nerve fascicle. Both the electric signal transmission devices 100 are inserted into the cut part of the nerve fascicle such that a first nerve cell functioning as an arranged cell is opposed to a cut section of the nerve fascicle.

The first nerve cell arranged on an electrode of the electric signal transmission device 100 extends an axon along the nerve fascicle into which the electric signal transmission device 100 is inserted (see, for example, Stephen J. A., et al., "Long Interfascicular Axon Growth from Embryonic Neurons Transplanted into Adult Myelinated Tracts," The Journal of Neuroscience, March 1994, 74 (3): 1596 to 1612). A synapse on the axon extending from the first nerve cell arranged on the electrode of the electric signal transmission device 100 is synapse-coupled to a second nerve cell that forms the nerve fascicle into which the electric signal transmission device 100 is inserted.

When the second nerve cell is stimulated in the hemisphere, active potential, which is an electric signal, is transmitted through the axon of the first nerve cell and the electric signal is transmitted to the electrode 11 of the electrode array 10. Consequently, the electric signal transmission device 100 is capable of receiving the active potential of the second nerve cell. When information is recorded in the hemisphere, the electrode 11 of the electrode array 10 of the electric signal transmission device 100 emits an electric signal. The electric signal emitted from the electrode 11 is sent to the second nerve cell in the brain via the first nerve cell arranged on the electrode.

REFERENCE SINGS LIST

10 . . . Electrode array, 20 . . . Cell retention membrane, 21 . . . Recess, 100 . . . Electric signal transmission device

The invention claimed is:

1. An electric signal transmission device operation method comprising receiving, by an electric signal transmission device opposed to an axon of a nerve cell inside a body, a first electric signal derived from the axon of the nerve cell inside the body, emitting a second electric signal by the electric signal transmission device, and thereby regenerating the axon of the nerve cell inside the body, wherein the electric signal transmission device comprises an electrode and a nerve cell disposed on the electrode and spaced from an end portion of the axon of the nerve cell inside the body, the end portion of the axon of the nerve cell inside the body is a cut part of the axon of the nerve cell inside the body, the electrode receives the first electric signal derived from the axon of the nerve cell inside the body, the electrode emits the second electric signal to the axon of the nerve cell inside the body, the nerve cell disposed on the electrode is different from the nerve cell inside the body, and the nerve cell disposed on the electrode induces a regeneration of the cut part of the axon of the nerve cell inside the body, and a synapse on an axon of the nerve cell disposed on the electrode is synaptically coupled to the axon of the nerve cell inside the body.

2. The electric signal transmission device operation method according to claim 1, wherein the electric signal transmission device further comprises a cell retention membrane in which a recess located on the electrode is provided, and the nerve cell disposed on the electrode is disposed in the recess of the cell retention membrane.

3. The electric signal transmission device operation method according to claim 1, wherein the axon of the nerve cell inside the body is included in a nerve fascicle.

4. The electric signal transmission device operation method according to claim 1, wherein the axon of the nerve cell inside the body is included in a central nervous system.

5. The electric signal transmission device operation method according to claim 4, wherein the axon of the nerve cell inside the body is included in a brain.

6. The electric signal transmission device operation method according to claim 4, wherein the axon of the nerve cell inside the body is included in a nerve fascicle connecting two hemispheres.

7. The electric signal transmission device operation method according to claim 1, wherein the axon of the nerve cell inside the body is included in a peripheral nervous system.

8. The electric signal transmission device operation method according to claim 1, wherein the electric signal transmission device is inserted into a nerve fascicle.

9. The electric signal transmission device operation method according to claim 1, wherein the nerve cell disposed on the electrode is a single cell.

* * * * *